US006846665B1

(12) United States Patent
Hörer et al.

(10) Patent No.: US 6,846,665 B1
(45) Date of Patent: Jan. 25, 2005

(54) METHOD OF PRODUCING A RECOMBINANT ADENO-ASSOCIATED VIRUS, SUITABLE MEANS FOR PRODUCING THE SAME AND USE THEREOF FOR PRODUCING A MEDICAMENT

(75) Inventors: Markus Hörer, Planegg Martinsried (DE); Michael Hallek, Schondorf (DE)

(73) Assignee: MediGene Aktiengesellschaft, Planegg/Martinsried (DE)

(*) Notice: Subject to any disclaimer, the term of this patent is extended or adjusted under 35 U.S.C. 154(b) by 0 days.

(21) Appl. No.: 09/913,240

(22) PCT Filed: Feb. 10, 2000

(86) PCT No.: PCT/EP00/01090

§ 371 (c)(1),
(2), (4) Date: Jan. 15, 2002

(87) PCT Pub. No.: WO00/47757

PCT Pub. Date: Aug. 17, 2000

(30) Foreign Application Priority Data

Feb. 10, 1999 (DE) .......................................... 199 05 501

(51) Int. Cl.[7] ........................ C12N 7/01; C12N 15/864; C12N 15/35
(52) U.S. Cl. ............................... 435/235.1; 435/320.1; 435/456; 435/465; 435/475; 536/23.72
(58) Field of Search .......................... 435/235.1, 320.1, 435/456, 465, 475; 536/23.72

(56) References Cited

U.S. PATENT DOCUMENTS

| | | | |
|---|---|---|---|
| 5,354,678 A | 10/1994 | Lebkowski et al. | |
| 5,789,390 A | 8/1998 | Descamps et al. | |
| 5,846,528 A | 12/1998 | Podsakoff et al. | |
| 5,858,351 A | 1/1999 | Podsakoff et al. | |

FOREIGN PATENT DOCUMENTS

| | | | |
|---|---|---|---|
| EP | 0 001 929 | 5/1979 | |
| EP | 0 148 605 | 7/1985 | |
| EP | 0 188 479 B1 | 7/1986 | |
| EP | 0 488 528 B1 | 6/1992 | |
| WO | WO 92/00092 | 1/1992 | |
| WO | WO 94/04196 | 3/1994 | |
| WO | WO 94/16716 | 8/1994 | |
| WO | WO 95/06738 | 3/1995 | |
| WO | WO 96/17947 | 6/1996 | |
| WO | WO 96/36364 | 11/1996 | |
| WO | WO 97/09441 | 3/1997 | |
| WO | 97/09441 | * 3/1997 | .......... C12N/15/86 |
| WO | WO 97/32988 | 9/1997 | |
| WO | WO 97/49824 | 12/1997 | |
| WO | WO 98/06746 | 2/1998 | |
| WO | WO 98/09657 | 3/1998 | |
| WO | 98/27204 | * 6/1998 | .......... C12N/15/00 |
| WO | WO 98/27204 | 6/1998 | |
| WO | WO 98/39420 | 9/1998 | |
| WO | WO 98/45462 | 10/1998 | |

OTHER PUBLICATIONS

Holscher et al (Journal of Virology 68:7169–7177, 1994).*
Holscher et al (Journal of Virology 69:6880–6885, 1995).*
Butz et al., "Transcriptional Control of Human Papillomavirus (HPV) Oncogene Expression: Composition of the HPV Type 18 Upstream Regulatory Region," *Journal of Virology* 67:6476–6486 (1993).
Chen et al., "High–Efficiency Transformation of Mammalian Cells by Plasmid DNA," *Molecular and Cellular Biology* 7:2745–2752 (1987).
Chiorini et al., "High–Efficiency Transfer of the T Cell Co–Stimulatory Molecular B7–2 to Lymphoid Cell Using High–Titer Recombinant Adeno–Associated Virus Vectors," *Human Gene Therapy* 6:1531–1541 (1995).
Gerard et al., "New Host Cell System for Regulated Simian Virus 40 DNA Replication," *Molecular and Cellular Biology* 5:3231–3240 (1985).
Holscher et al., "High–Level Expression of Adeno–Associated Virus (AAV) Rep78 or Rep68 Protein is Sufficient for Infectious–Particle Formation by a *rep*–Negative AAV Mutant," *Journal of Virology* 69:6880–6885 (1995).
Hoppe–Seyler et al., "Cellular Control of Human Papillomavirus Oncogene Transcription," *Molecular Carcinogenesis* 10:134–141 (1994).
Horer et al., "Mutational Analysis of Adeno–Associated Virus Rep Protein–Mediated Inhibition of Heterologous and Homologous Promoters," *Journal of Virology* 69:5485–5496 (1995).
Laughlin et al., "Cloning of Infectious Adeno–Associated Virus Genomes in Bacterial Plasmids," *Gene* 23:65–73 (1983).
Lebkowski et al., "Adeno–Associated Virus: A Vector System for Efficient Introduction and Integration of DNA into a Variety of Mammalian Cell Types," *Molecular and Cellular Biology* 8:3988–3996 (1988).

(List continued on next page.)

*Primary Examiner*—Mary E. Mosher
(74) *Attorney, Agent, or Firm*—Clark & Elbing LLP

(57) ABSTRACT

The present invention relates to a method for producing a recombinant adeno-associated virus (rAAV), in which at different times a helper construct and also a vector construct are introduced into a suitable cell, and preferably the helper construct does not comprise, in particular with the exception of the AAV promoters, any nucleic acid sequences to which at least a Rep protein can essentially specifically bind and preferably the vector construct comprises ITR sequences in flop orientation. The recombinant adeno-associated viruses produced according to the method of the invention are suitable in particular for producing a tumor cell into which additionally nucleic acids coding for GM-CSF and B7.2 has been introduced, which in turn can be used in the form of a medicament for the treatment of cancers.

27 Claims, 8 Drawing Sheets

OTHER PUBLICATIONS

McCarty et al., "Interaction of the Adeno–Associated Virus Rep Protein with a Sequence Within the A Palindrome of the Viral Terminal Repeat," *Journal of Virology* 68:4998–5006 (1994).

Muzyczka, "Use of Adeno–Associated Virus us a General Transduction Vector for Mammalian Cells," *Current Topics in Microbiology and Immunology* 158:97–129 (1992).

Rudy et al., "Differential Function of CD80– and CD86– Transfected Human Melanoma Cells in the Presence of IL–12 and IFN–γ," *International Immunology* 9:853–860 (1997).

Samulski et al., "Helper–Free Stocks of Recombinant Adeno–Associated Viruses: Normal Integration Does Not Require Viral Gene Expression," *Journal of Virology* 63:3822–3828 (1989).

Samulski et al., "A Recombinant Plasmid from Which An Infectious Adeno–Associated Virus Genome Can Be Excised in Vitro and Its Use to Study Viral Replication," *Journal of Virology* 61:3096–3101 (1987).

Samulski et al., "Cloning of Adeno–Associated Virus into pBR322: Rescue of Intact Virus from the Recombinant Plasmid in Human Cells," *Proc. Natl. Acad. Sci. USA* 79:2077–2081 (1982).

Srivastava et al., "Nucleotide Sequence and Organization of the Adeno–Associated Virus 2 Genome," *Journal of Virology* 45:555–564 (1983).

Uhlmann et al., "Antisense Oligonucleotides: A New Therapeutic Principle," *Chemical Reviews* 90:544–584 (1990).

Vincent et al., "Replication and Packaging of HIV Envelope Genes in a Novel Adeno–Associated Virus Vector System," *Vaccines* 90:353–359 (1990).

Weger et al., "Control of Adeno–Associated Virus Type 2 Cap Gene Expression: Relative Influence of Helper Virus, Terminal Repeats, and Rep Proteins," *Journal of Virology* 71:8437–8447 (1997).

* cited by examiner

Fig. 1

Day 1: Culturing of HeLa-t cells in DMEM medium with fetal calf serum (FCS)

Day 2: Calcium phosphate transfection with helper plasmid pUC "rep/cap"(RBS)Δ37

Day 3: Calcium phosphate transfection with vector plasmid pAAV-(B7.2/GM-CSF)

Day 4: Infection with adenovirus Ad-5

Day 5: Replacing of culture medium with serum-free DMEM medium

Day 8 ff.:
1. Harvesting of cell pellet and supernatant
2. Preparation of crude lysate
3. Separation of rAAV particles from adenovirus by means of filtration
4. Concentration of rAAV particles by means of ultrafiltration
5. Transfection of autologous melanoma cells with rAAV particles
6. Irradiation of transduced melanoma cells
7. Treatment of patient with irradiated and transduced melanoma cells Fig. 2
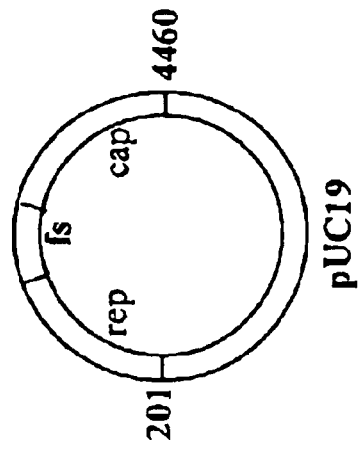
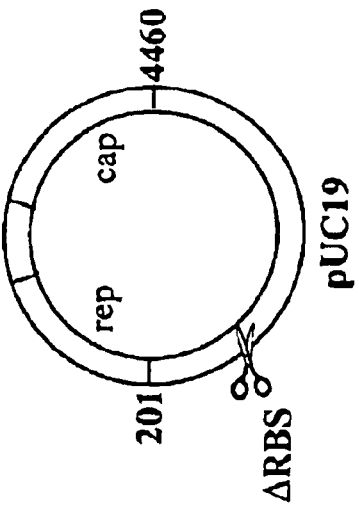
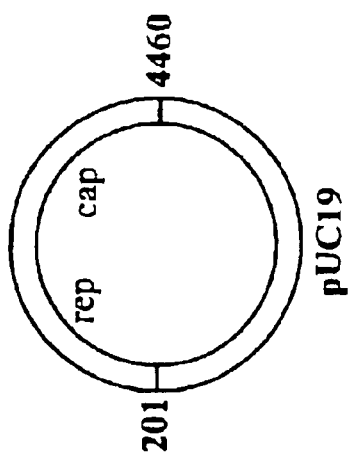
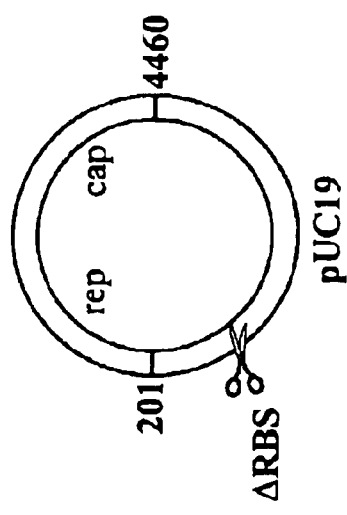

Fig. 4
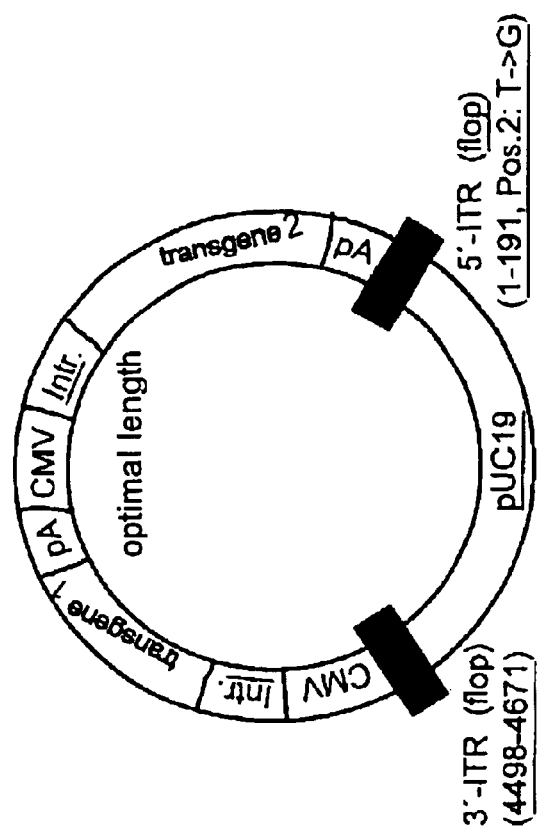
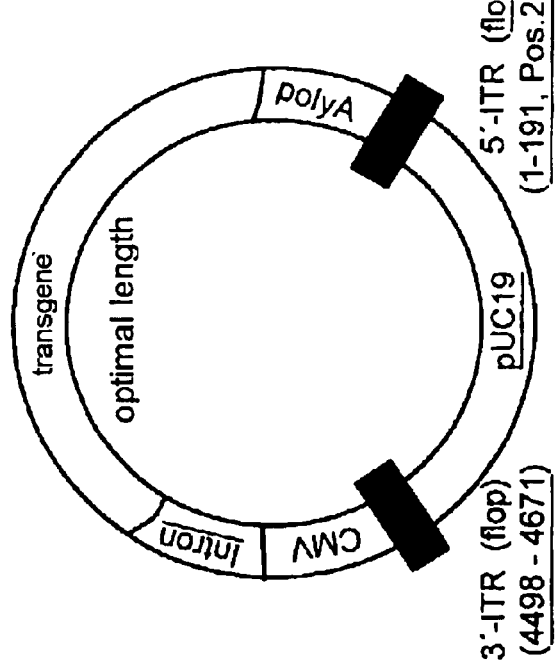

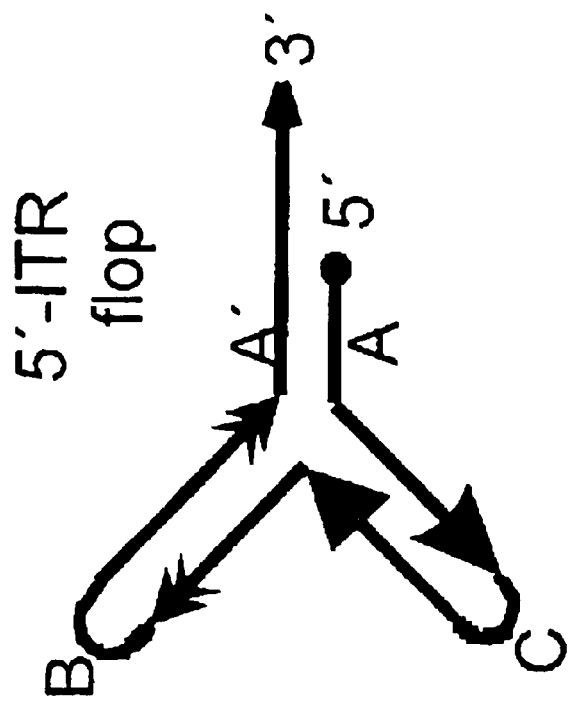
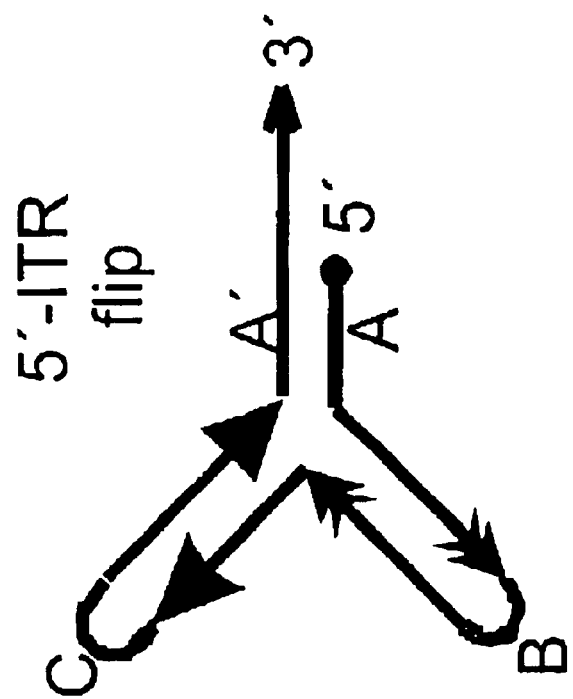
Fig. 5

Fig. 6    pUC"Rep68,52,40Cap"(RBS)Δ37

METHOD OF PRODUCING A RECOMBINANT ADENO-ASSOCIATED VIRUS, SUITABLE MEANS FOR PRODUCING THE SAME AND USE THEREOF FOR PRODUCING A MEDICAMENT

CROSS REFERENCE TO RELATED APPLICATIONS

This application is the U.S. National Stage of International Application No. PCT/EP2000/01090, filed Feb. 10, 2000, which claims the benefit of German Application No. 19905501.7, filed Feb. 10, 1999.

The present invention relates to a method for producing a recombinant adeno-associated virus (rAAV), in which at different times a helper construct and also a vector construct are introduced into a suitable cell, and preferably the helper construct does not comprise, in particular with the exception of the AAV promoters, any nucleic acid sequences to which at least a Rep protein can essentially specifically bind and preferably the vector construct comprises ITR sequences in flop orientation. The recombinant adeno-associated viruses produced according to the method of the invention are suitable in particular for producing a tumor cell into which additionally nucleic acids coding for GM-CSF and B7.2 has been introduced, which in turn can be used in the form of a medicament for the treatment of cancers.

For the genetic modification of therapeutically active cells which, for example, may be used as tumor vaccines, suitable methods for transferring nucleic acids, i.e. DNA or RNA, which cause genetic modification of the cell are necessary. The nucleic acids to be transferred are frequently also referred to as "transgenes", even if they themselves do not function as a gene, for example in the case of the "antisense nucleic acids". Besides the direct gene transfer of "naked nucleic acids" genetically modified viruses have also proved suitable for the gene transfer. At present, retroviruses, adenoviruses or adeno-associated viruses (AAV) inter alia are being genetically modified, in order to be able to use them as carriers (viral vectors) of the transgene(s) for the gene transfer. An essential point of view when developing suitable viral vectors are safety aspects in connection with application of said vectors in gene therapy. For this reason, generally "replication-deficient" viruses are developed, i.e. viruses which, although they can infect a cell and transfer the transgene(s) into the cell, are, however, unable to propagate themselves in said cell. This is achieved, for example, by deleting genes important for virus propagation, for example the genes coding for structural proteins, and, where appropriate, incorporating in their place the transgene(s). For the production of larger amounts of non-propagatable viruses, suitable for use in gene therapy, "helper genes" which compensate the defect of a non-propagatable virus in the cell are necessary.

AAV, for example, is a human virus which either is present in the form of a provirus integrated into the genome or causes a lytic infection. Therefore, AAV is of interest as a general transduction vector of mammalian cells. AAV is a member of the parvovirus family of which six different serotypes AAV-1, AAV-2, AAV-3, AAV-4, AAV-5 and AAV-6 are known at present. AAV-2, for example, contains a single-stranded linear DNA of approx. 4.7 kilo bases (kb) in length. The viral particles which are composed of three viral proteins, VP1, VP2 and VP3, contain a strand of viral DNA which has either one polarity (+) or the other polarity (−).

Using AAV as viral transduction vector in general requires relatively large amounts of recombinant AAV particles. An advantageous method for producing relatively large amounts of rAAV particles is cotransfection of a eukaryotic cell with two recombinant AAV plasmids in the form of a mixture and infection with a helper virus (Chiorini, J. A. et al. (1995) Human Gene Therapy, 6, 1531). The first recombinant AAV plasmid contains the transgene(s) which is (are) bordered, i.e. flanked, by the two ITR regions. According to the present invention, said AAV plasmid is also referred to as vector construct. The second recombinant AAV plasmid contains the AAV genes which are required for producing the particles (rep and cap genes). According to the present invention, this vector is also referred to as helper construct. The absence of the ITR regions in the helper construct ought to prevent packaging of the rep and cap genes into AAV particles and thus the formation of unwanted wild type AAV. Subsequently, suitable cells which are permissive, i.e. accessible, both for the recombinant AAV construct and for the helper virus are transfected with the two AAV constructs. After infecting the transfected packing cells with adenoviruses, the AAV genes are expressed, transgene DNA is replicated and the recombinant AAV particles (rAAV particles) are packaged and assembled. The rAAV particles contain the transgene(s), flanked on both sides by the ITR regions, in the form of single-stranded DNA. At the same time, the helper virus replicates in said cells and, in the case of adenoviruses as helper viruses, this generally results in lysis and death of the infected cells after a few days. The rAAV particles and also the helper viruses formed are in this context partially released into the cell culture supernatant or remain in the lysed cells. A review on the use of AAV as general transduction vector for mammalian cells is given, for example, by Muzyczka, N. in Current Topics in Microbiology and Immunology, 158, 97 (1992).

A substantial disadvantage of the production of rAAV particles is the accompanying formation of wild type AAV and the presence of helper viruses. With regard to safety in the use of recombinant AAV particles, for example in gene therapy, it is, however, necessary that the preparations are essentially free of helper viruses and wild type AAV for the following reasons: adenoviruses as helper viruses are lytic to cells and cause cellular immune responses against adenoviral proteins. In addition, adenoviruses are human pathogens, since they provoke unspecific cold symptoms. Replication-competent wild type AAVs can propagate in the presence of a helper virus such as, for example, adenovirus or HSV and can spread in the organism, without being pathogenic, however. In addition, under such conditions rep and cap genes would be expressed, which in turn would amplify rAAV genomes in the same cell and package into new rAAV particles. This would make it possible for the rAAV genes to spread in the entire organism.

It is, therefore, an object of the present invention to provide a method and suitable constructs which essentially prevent the formation of wild type AAV.

It has now been found that transfection of cells with one or more helper constructs (first construct) and a vector construct (second construct) at different times, independently of whether the helper construct or the vector construct is transfected first, can essentially achieve the same packaging efficiencies as the simultaneous cotransfection of both constructs, it being possible, however, owing to a reduction in the homologous or non-homologous recombination of the two constructs, to reduce possible formation of wild type AAV markedly, in particular approx. 10-fold. Preferably, the cells are transfected first with the helper construct and then with the vector construct, since it was surprisingly possible to increase the packaging efficiency by a factor of approx. 1.5–3.

The present invention therefore relates to a method for producing a recombinant adeno-associated virus, in which at different times one or more helper constructs comprising nucleic acid sequences coding for at least one Rep protein, preferably for Rep 68, Rep 52 and Rep 40, in particular for Rep 68 and Rep 52 and for the Cap proteins and also a vector construct comprising one or more nucleic acids which are heterologous to AAV and are flanked by ITR sequences are introduced into a suitable cell.

The rep and cap genes here may be located on one and the same helper plasmid or on a plurality of helper plasmids, for example a helper plasmid codes for at least one of the Rep proteins and a second helper plasmid codes for the Cap protein. The advantage of using a plurality of helper plasmids is that a plurality of recombination events are required for the recombination of all plasmids to give unwanted wt AAV, for example a recombination event between the helper plasmids and another between the recombinant helper and the vector plasmid. A plurality of required recombination events thus makes generation of unwanted wt AAV during packaging of the rAAV vectors even more improbable.

Suitable cells are generally cells which are permissive for said constructs, preferably mammalian cells, for example COS-7, HeLa, C33a or 293 cells. A suitable method for introducing the constructs is, for example, the calcium phosphate transfection method in classical or modified form (Chen, C. & Okayama, H. (1987) Mol. Cell. Biol., 7 (8), 2745). An advantage of the modified calcium phosphate transfection method is that it is possible in combination with the method of the invention to achieve reproducibly very high transfection efficiencies of up to 100% transfected cells.

According to the present invention, nucleic acid generally means DNA or RNA and variants thereof, which can be packaged in the form of AAV capsids and are suited to being introduced into a suitable cell. Examples of variants are listed, for example, in Uhlmann, E. & Peyman, A. (1990) Chemical Reviews, 90, 543–584, No. 4.

In a preferred embodiment, the cells are purified after introducing the first construct and before introducing the second construct. Purification may be carried out, for example, in a simple manner by changing the medium. However, it is advantageous to rinse the cells before the second step with a solution, for example PBS buffer (phosphate-buffered sodium chloride solution), in order to remove essentially completely remainders of the first construct, which may not have been internalized.

The rAAV particles are subsequently produced either by adding suitable helper viruses such as, for example, adenoviruses, herpes viruses, vaccinia viruses, or in the presence of helper genes thereof. The helper genes of adenoviruses are E1A, E1B, E4, E2A and VA. Alternatively, it is also possible to use a cell which expresses helper gene products constitutively, for example the 293 cell which expresses the E1A gene constitutively. The gene products E1B and E4 here serve to enhance AAV mRNA accumulation and the gene products E2A and VA serve to enhance AAV mRNA splicing and translation. The use of a helper virus, for example adenovirus Ad-5, instead of the individual helper genes is particularly advantageous, since this most likely corresponds to the authentic situation of AAV propagation in the presence of helper viruses and packaging of recombinant AAV particles is thus very efficient.

The time differences between the individual steps preferably and independently of one another are at least approx. 1 hour, preferably at least approx. 12 hours, in particular at least approx. 1 day, especially approx. 1 to 2 days.

Subsequently, the rAAV particles can advantageously be produced in serum-free medium such as DMEM without loss of rAAV and, as a result, a purification step in the further purification of the rAAV particles can be dispensed with, since there is essentially no contamination of protein, for example from a 10% serum fraction.

The production time of the cells is about 4 to 6 days, and, owing to adenovirus-mediated cell lysis, rAAV vectors are released into the supernatant from about the third day onward. There is, however, always the possibility of finding a proportion of rAAV particles in the cells, too. The proportion of rAAV capsids which are released into the medium is generally up to 90%, with approx. at least 10% remaining in the cells. It is therefore advantageous to harvest and purify the rAAV particles both from the cells and from the supernatant.

Subsequent purification may be carried out, for example, via a CsCl gradient (Chiorini, J. A. et al. (1995), supra) or preferably with the aid of a filtration (see WO 98/39420). After purification an essentially helper virus-free preparation of rAAV particles is obtained. The rAAV particles can then be concentrated by means of ultrafiltration and stored.

The helper construct(s) used for the method of the invention comprise(s) nucleic acid sequences coding for at least one Rep protein and/or the Cap proteins. Known Rep proteins are Rep 78, Rep 68, Rep 52 and Rep 40. Known Cap proteins are VP1, VP2 and VP3. The genes thereof and also the ITR sequences can be isolated from wild type AAVs which are in general available in the form of clones. Thus for example clone pSM620 is described in Samulski, R. J. et al. (1982) Proc. Natl. Acad. Sci. USA, 79, 2077, clone pAV1 in Laughlin, C. A. et al. (1983) Gene, 23, 65 or clone sub201 in Samulski, R. J. (1987) J. Virol. 61, 3096.

In a preferred embodiment of the present invention, the rep and cap genes are controlled by their natural promoters p5, p19 and p40. It has turned out that not only the naturally occurring AAV promoters contain Rep binding sites but Rep binding sites are also present in other parts of the construct for example in the vector backbone of vector pUC19 or vector pBR322 (McCarty, D. M. et al. (1994) J. Virol., 68, 4988), which binding sites may be responsible for non-homologous recombination and thus for the formation of wild type AAV.

The large Rep proteins Rep 78 and Rep 68, for example, are capable of forming protein complexes which can bind a plurality of RBS sequences simultaneously. Owing to the endonuclease and helicase activities of Rep, recombination of two nucleic acid sequences in the region of RBS sites is therefore possible.

The invention therefore also relates to one or more, preferably two, helper constructs comprising nucleic acid sequences coding for at least one Rep protein and for the Cap proteins, and the helper construct(s) preferably thus does (do) not comprise, with the exception of the AAV promoters, any nucleic acid sequences to which at least one Rep protein, preferably Rep 78 and/or Rep 68, can essentially specifically bind. The RBS consensus sequence is described, for example, in McCarty, D. M. et al. (1994), supra and is: CGCTTCCTCGCTCACTGA (SEQ. ID NO: 1).

Binding of Rep proteins to Rep binding sites (RBS) is reduced or prevented, for example, by the fact that the three known RBS in the rep promoters p5 and p19 have been mutated individually or in various combinations, preferably without altering the Rep amino acid sequences as a result of this.

In a particularly preferred embodiment, the Rep proteins are Rep 68, Rep 52 and Rep 40, but not Rep 78, because surprisingly it has been found that besides Rep 52, Rep 40 and the three Cap proteins VP1, VP2 and VP3 additional expression only of Rep 68 is sufficient for packaging AAV vectors. The advantage of said Rep 78-deficient helper constructs is that this Rep protein which is most toxic for the packaging cells is not expressed at all. Furthermore it has been found that Rep 78 has the greatest activity of inhibiting cellular processes, for example transcription, among the Rep proteins. Using this helper construct therefore makes it possible, owing to the absence of Rep 78, to increase packaging efficiency. Likewise, production of stable cell lines which express Rep and Cap proteins is simplified, because the most toxic protein Rep 78 is not expressed. Both Rep 68 and Rep 78 are expressed in the natural system by promoter p5. Using this Rep 78-deficient helper construct is furthermore advantageous, because Rep 68 represents the stronger transactivator of AAV promoters p19 and p40 in adenovirus-infected cells, compared with Rep 78 (Hörer et al. (1995) J. Virol. 69, 5485–5496; Weger et al. (1997) J. Virol. 71, 8437–8447). As a result, using this Rep 78-deficient helper construct leads to increased expression of the smaller Rep proteins Rep 40 and Rep 52 and of the capsid proteins and therefore to the desired higher packaging efficiency. Finally, owing to duplication of the rep gene or parts of the rep gene, which is required for cloning Rep 78-deficient helper constructs, the oversize of the AAV genes prevents formation of wt AAV after recombination with the vector construct.

Within the scope of the present invention it is possible to use the helper constructs of the invention and in particular the Rep 78-deficient helper construct not only for transient transfection experiments which result in lysis and death of the transfected cell, but also for permanent (=stable) expression of the Cap and Rep proteins, which is achieved by targeted or random integration of the helper constructs into the genome of the host cell. Here again, particular preference is given to expressing the proteins Rep 68, Rep 52 and Rep 40 due to the toxic action of Rep 78.

Another possibility to introduce the helper constructs of the invention into a host cell besides the transient and stable transfections already described is infection using a virus as helper construct vehicle. For this, the virus interacts with the host cell via its cell surface (adhesion), and subsequently the nucleic acids packaged in the virus, in particular the helper constructs of the invention and particularly preferably the Rep 78-deficient helper construct, are taken up into the host cell (penetration). It is possible, for example, to produce a recombinant adenovirus by replacing the E1A region by a helper construct of the invention in E1A-complementing cells.

In a further preferred embodiment, the helper construct(s) comprise(s) between the nucleic acid sequence coding for at least one Rep protein and the nucleic acid sequence coding for the Cap proteins an additional nucleic acid sequence which impairs packaging of the helper construct into an AAV capsid. The additional nucleic acid sequence here serves to increase the overall length of the AAV construct, as a result of which an efficient packaging is impaired or even prevented. Prevention of packaging is generally achieved if the wild type AAV DNA size of 4680 base pairs is markedly exceeded. This is preferably achieved if the additional nucleic acid sequence is at least approx. 300 nucleotides, in particular at least approx. 500 nucleotides, especially at least approx. 600 to approx. 700 nucleotides, in length.

Owing to the overlap of rep and cap genes in wild type AAV, the preparation of a helper construct having said additional nucleic acid can be prepared, for example, as follows: in a first step, the AAV sequence from 1691 to 2328, which contains the Rep C terminus and the AAV p40 promoter including cap sequences and all regulatory sequences essential for p40, is duplicated and cloned behind the stop codon for the spliced rep versions (position 2329). Subsequently, the p40 promoter in the rep gene is destroyed without altering the Rep amino acid sequence. This can be guaranteed by mutation of the p40 TATA box. In total, the following AAV nucleotides can be modified for the cloning steps without altering the Rep and Cap amino acid sequences: 1693 (T→A), 1694 (T→G), 2330 (G→C), 2331 (G→T), 2332 (G→A), 1625 (C→T), 1628 (A→G), 1826 (A→C), 1827 (A→T) and 1828 (G→C).

In order to further reduce the probability of wild type AAV formation during rAAV production, it is advantageous to prepare a helper construct which does not comprise any nucleic acid sequences which are homologous to the vector construct and allow homologous recombination. This may be carried out, for example, by amplifying AAV nucleotides 190 to 1060 from wild type AAV by means of a polymerase chain reaction (PCR). In this connection, the 5' primer should be chosen such that a singular XbaI cleavage site is introduced at position 199. It is then possible to cut the PCR fragment with XbaI and BamHI and to clone it into a vector, for example pUC19, which has been cut analogously. Position 199 in the AAV genome ensures that all important p5 promoter elements are present in the helper plasmid. Subsequently, wild type AAV is cut with BamHI and SnaBI and the insert fragment is then cloned into the BamHI and SmaI positions of the intermediate. In this way it is possible, for example, to prepare the helper construct denoted pUC "Rep/Cap". This helper construct contains the AAV sequences 201 to 4497, while the vector construct carries the AAV sequences 1 to 191 (left ITR) and 4498 to 4671 (right ITR). In this way, there are no longer any homologous AAV sequence overlaps in the constructs.

In a further preferred embodiment, it is possible, for example in pUC "Rep/Cap", to delete up to approx. 37 bases of the 3' end of the AAV genome, preferably the AAV-2 bases 4461–4497, which are not required for optimal expression of the AAV rep and cap genes. According to the present invention, the resulting helper construct is denoted pUC "Rep/Cap" Δ37 and contains the minimized AAV sequence from position 201 to 4460.

The Rep 78-deficient helper construct pUC"Rep68,52, 40Cap"(RBS)Δ37 (cf. FIG. 6) was prepared by cloning the AAV sequences from nucleotide 201 to nucleotide 4497 including the deletion of the intron sequence and also from nucleotide 658 to nucleotide 4460 into the bacterial expression plasmid pUC19, in which process the binding sites for the Rep protein in the present sequence were deleted. By applying this strategy, two rep genes and also at least two cap genes having, in each case, an own poly(A) sequence for transcription termination are arranged one behind the other. Starting from the first section (AAV sequence nucleotide 201 to nucleotide 4497) the Rep proteins Rep 68 and Rep 40 and also the Cap proteins VP2 and VP3 can be expressed, whereas, starting from the second section (AAV sequence nucleotide 658 to nucleotide 4460), the Rep proteins Rep 52 and Rep 40 and also the Cap proteins VP1, VP2 and VP3 are expressed. Thus, in total, all AAV 2-proteins with the exception of Rep 78 are encoded.

The likewise Rep 78-deficient helper construct pUC"ΔRep78Cap"(RBS)Δ37 (cf. FIG. 7) was prepared by cloning said AAV sequences (nt 201–2310; nt 658–4460 including the deletion of the intron sequence) likewise into the bacterial expression plasmid pUC19. During the process, the binding sites for the Rep protein in the plasmid sequence were again deleted. In this way, the rep gene was partially duplicated. The helper construct obtained in this way contains only one poly(A) sequence so that all mRNA transcripts have the same 3' end. Starting from the first section (AAV sequence nucleotide 201 to nucleotide 2310), the Rep proteins Rep 68 and Rep 40 can be expressed, whereas, starting from the second section (AAV sequence nucleotide 658 to nucleotide 4460), the Rep proteins Rep 52 and Rep 40 and also the Cap proteins VP1, VP2 and VP3 are expressed. This vector construct, too, in total codes for all AAV-2 proteins with the exception of Rep 78.

According to the present invention, it is also possible to replace independently of one another the homologous AAV promoters which control expression of the Rep and Cap proteins with a heterologous promoter and/or enhancer. It is generally possible to use the same promoters or enhancers which control also expression of the heterologous nucleic acid sequences in the vector construct (transgene), as described below in more detail. Particular preference is given to the HPV 18 enhancer which is highly active especially in HeLa and C33a cells (Butz, K. & Hoppe-Seyler, F. (1993) J. Virol., 67, 6476–6486; Hoppe-Seyler, F. & Butz, K. (1994) Mol. Carcinog., 10, 134–141).

According to the present invention, a helper construct is obtained which is optimized for the method of the invention and which comprises firstly the rep genes coding for the replication proteins and secondly the cap genes coding for the coat proteins. A particularly preferred helper construct of the invention is replication-incompetent, since it contains no ITR sequences. In addition, the helper construct is optimized in that it is possible to reduce or essentially prevent formation of wild type AAV, owing to the advantageous modifications described above. Generally, however, the separation of the ITR sequences from the AAV promoters leads to deregulation of rep and cap expression in the helper construct.

Advantageously, modifications in the vector construct are to be carried out such that they essentially cannot exert any negative influence on the packaging efficiency of the vector constructs but, on the contrary, stabilize the vector constructs, to reduce or essentially avoid unwanted recombination events and/or lead to an increase in the rate of expression of the incorporated transgenes.

It is known that the AAV-2 ITR sequences which are 145 base pairs in length are composed of a large palindrome (A) and two smaller internal palindromes (B and C). The first 125 bases of the ITR sequence here form a hairpin structure of T-shape (see, for example, Muzyczka, N. (1992), supra). The terminal sequence may be present here in one of two configurations. In the first configuration, also called "flip", the B palindrome is closer to the 3' end and in the second configuration, also called "flop", the C palindrome is closer to the 3' end (see also Srivastava, A. et al. (1983) J. Virol. 45(2), 555).

Surprisingly, it has now been found that a flop-flop orientation of both ITR sequences in the vector constructs is distinctly more stable than a flip-flop or flip-flip orientation. In addition, the flop-flop orientation is less frequently susceptible to unwanted recombination events than the flip-flop orientation.

The present invention therefore further relates to a vector construct comprising one or more nucleic acids which are heterologous to AAV and are flanked by ITR sequences, the ITR sequences being present in flop orientation.

In a preferred embodiment, expression of the heterologous nucleic acids is controlled by a promoter heterologous to AAV. Surprisingly, it has been found here that the rate of expression can be increased by orientation of the heterologous promoter toward the 3' located ITR sequence.

Suitable promoters are all promoters homologous and, preferably, heterologous to AAV. Promoters homologous to AAV are the promoters p5, p19 and/or p40, and suitable promoters heterologous to AAV are all constitutively active or inducible promoters which are active in eukaryotic cells, preferably mammalian cells. These include, for example, the SV40-promoter (Samulski, R. J. (1989) J. Virol. 63, 3822), SV40ori-enhancer, CMV-promoter/enhancer (Vincent, K. A. et al. (1990) Vaccine, 90, 353) or LTR-promoter (Lebkowski, J. S. (1988) Mol. Cell. Biol. 8, 3988). Particularly preferred is the CMV promoter/enhancer.

For efficient packaging of the vector constructs into AAV capsids with the aid of the helper constructs, a vector construct size of not substantially below or above approx. 4700 base pairs ±5% is advantageous. It is possible, for example, to cut the plasmid pAV2 (Laughlin, C. A. et al. (1983) supra) with the restriction endonuclease BglII and to subclone the AAV sequences obtained by this into the vector pUC19 (Yannish-Perron, C. et al. (1985) Gene, 33, 103). This is carried out, for example, by cutting pUC19 with BamHI and ligating it directly with the BglII fragment of pAV2. Control sequencing of the ITRs has proved that the left ITR is completely intact except for a base exchange at position 2 (T→G), whereas the right ITR lacks 8 terminal bases. However, this does not adversely affect the replication ability of the construct, since the defects can be repaired during replication of the AAV genome so that the constructs can carry two intact ITRs.

Subsequently, the AAV sequences 192 to 4497 can be removed and be replaced by a CMV polyA expression cassette. To this end, for example, PpuMI and EcoRV cleavage sites are introduced by double-strand mutageneses into the vector pCI (Promega GmbH, Mannheim, Germany) in front of the CMV promoter/enhancer or after the polyA site, the CMV polyA expression cassette is cut out and cloned directly into the vector construct cut with PpuMI and SnaBI. The optimal orientation of the expression cassette can be determined, for example, with the aid of the luciferase reporter gene. As already mentioned above, the rate of expression is highest if the heterologous promoter, in particular the CMV promoter/enhancer, is orientated toward the right ITR, i.e. toward the 3' located ITR sequence.

The helper constructs and/or vector constructs of the invention are particularly preferably suitable for producing recombinant AAV particles in the method of the invention. The following method has proved particularly advantageous here:

Firstly, suitable cells, for example HeLa cells are seeded in a preferred amount of approx. $1-2 \times 10^8$ cells into a medium with approx. 10% serum. Preferably on the following day, the cells are transfected with the helper construct, in particular with the aid of the calcium phosphate transfection method. The cells are then, preferably on the following day, rinsed with buffer, for example PBS buffer, and provided with fresh medium with approx. 10% serum. At the same time or shortly thereafter, the cells are transfected with preferably the same amount of vector construct. After some time, preferably on the following day, the cells are infected with helper viruses, preferably with adenoviruses, for example Ad-5. Preferably on the following day, the medium is again replaced with serum-free medium. The cells are then incubated, for example for a further three days, before the rAAV particles can be harvested from the cells and the medium supernatant.

A substantial advantage of the method of the invention is that a substantial reduction in the recombination of both constructs to give pseudo wild type AAV and also a packaging efficiency improved by a factor of 1.5–3 can be achieved. The yield of rAAV particles is approx. $10^{12}$ to $10^{13}$ and the yield of transducing rAAV particles at at least $10^9$–$10^{10}$. Another substantial advantage of the method of the invention is a substantially easier subsequent purification of the rAAV particles, in particular since, due to the exchange with serum-free medium, there is essentially no serum-containing medium with an unwanted protein fraction in the mixture.

According to the present invention it is possible to use as heterologous nucleic acid sequence essentially any coding and also noncoding nucleic acid sequence, for example genes coding for pharmaceutically active proteins such as, for example, erythropoietin (see e.g. EP 0 148 605 B1) or insulin (see e.g. EP 0 001 929 B1) or the genes coding for blood clotting factors, interferons, cytokines, hormones, growth factors, e.g. IL-2, IL-4, IL-12, p53 or γ interferon (see e.g. WO 94/16716), antibodies, etc., or "antisense oligonucleotides" as an example for noncoding nucleic acids. Preference is given to introducing one or more heterologous nucleic acid sequence(s) into a replication-deficient vector construct. Using replication-deficient vectors preferably involves working close to the saturation concentration of helper and vector construct in the cell. An example of a preferred amount of helper and vector construct is approx. 3.5–4 mg of construct for approx. 2–3×$10^8$ cells.

However, when using genes coding for pharmaceutically active proteins such as, for example, the above-mentioned proteins, it is generally also possible, in particular for the helper plasmid, to use self-replicating constructs which carry, for example, the SV40ori, preferably when the chosen transfection method makes saturation with the individual constructs impossible. It is in particular preferred to use constructs which comprise both SV40ori nucleic acid sequences (Mellon et al. (1981) Cell, 27, 279–288) and nucleic acid sequences coding for the SV40 T antigen (Gerard, R. D. & Gluzman, Y. (1985) Mol. Cel. Biol., 5, 3231–3240), since, as a result, a replication is achieved independently of cells stably expressing T antigen, such as COS-7 for example. Likewise it is possible to incorporate into the helper and/or vector plasmids also other known sequences for plasmid replication, such as, for example, the viral replication origin oriP of EBV (Epstein Barr Virus) or the expression cassette for the EBV replication protein EBNA.

WO 98/06746, for example, discloses that a genetically modified melanoma cell line expressing, for example, GM-CSF could be used as vaccine. WO 94/16716 discloses the use of a recombinant virus in cancer therapy using at least one cytokine, for example GM-CSF or B7 and/or a tumor-associated antigen. The B7 gene here refers to the "B7.1" gene. WO 94/04196 discloses a DNA construct for the treatment of tumors, which encodes a cytokine and additionally B7 which, here too, means B7.1. WO 92/00092 discloses the nucleic acid sequence coding for B7.1, WO 94/03408 and WO 95/06738 disclose the nucleic acid sequence coding for B7.2, and EP-B1-0 188 479 discloses the nucleic acid sequence for GM-CSF.

In connection with the vector construct of the invention the use of B7.2 is particularly advantageous, since in vitro studies have shown that, in contrast to B7.2, interferon-gamma or IL-12 have inhibitory effects in connection with B7.1 on the activation of T lymphocytes (Rudy et al. (1997) int. Immunol, 9, 853). In the presence of a second transgene coding for GM-CSF, the tumor-destroying action of a B7 molecule (B7.1 or B7.2) can be increased.

The present invention therefore further relates to a tumor cell, preferably a melanoma cell, into which a heterologous nucleic acid sequence coding for GM-CSF and B7.2 has been introduced, and to the use thereof as medicament, in particular for the treatment of cancers, especially of malignant cancers such as melanomas.

Owing to easier manipulation, particular preference is given to "double vectors" which contain both the nucleic acid sequence coding for GM-CSF and the nucleic acid sequence coding for B7.2. The use of double vectors in particular reduces the number of packaging processes. Surprisingly, the double vectors of the invention allow efficient expression of both transgenes, which is comparable with that of coinfection with two single vectors.

Preferably, a primary tumor, in particular a freshly isolated primary tumor, or an established proliferating tumor cell line is transduced with a recombinant AAV construct according to the present invention. Prior to the use as tumor vaccine, preferably before transduction, the tumor cells are usually irradiated, for example with a total dose of approx. 100 Gy to 300 Gy, in order to destroy the tumor cell without, however, losing its essential immunostimulating properties. Subsequently, preferably three times approx. $1 \times 10^6$ to approx. $1 \times 10^9$ tumor cells, preferably melanoma cells, in particular approx. $1 \times 10^6$ to approx. $1 \times 10^7$ tumor cells, for example approx. $3 \times 10^6$ tumor cells, are administered to the patient. The tumor cells (primary tumor or tumor cell line) may come either from the treated patient (autologous) or from other patients (allogeneic).

The constructs of the invention may also generally be used for the treatment of any disorders, preferably of tumors such as, for example, tumors of the ovary, mamma, colon, prostate, bronchi, head and/or neck, in addition to the malignant melanoma as already described in more detail above. Suitable therapeutic genes are the genes described above by way of example. Besides ex vivo modification of cells removed from the patient, such as tumor cells for example, using the constructs of the invention according to, preferably, the method of the invention, the patient may also be treated in vivo with the aid of the constructs of the invention (see e.g. U.S. Pat. No. 5,858,351 or U.S. Pat. No. 5,846,528).

The following figures and examples are intended to illustrate the invention in more detail without restricting it:

DESCRIPTION OF THE FIGURES

FIG. 1 shows an overview of the individual process steps for producing rAAV particles and the use thereof for producing an autologous vaccine for the treatment of melanomas.

FIG. 2 diagrammatically shows a selection of the helper constructs of the invention.

FIG. 4 diagrammatically shows single and double expression vectors.

FIG. 5 diagrammatically shows the 5' located ITR sequence of the AAV vector constructs with flip and flop configurations.

EXAMPLES

1. Revitalization of HeLa-t cells

Figure 3:
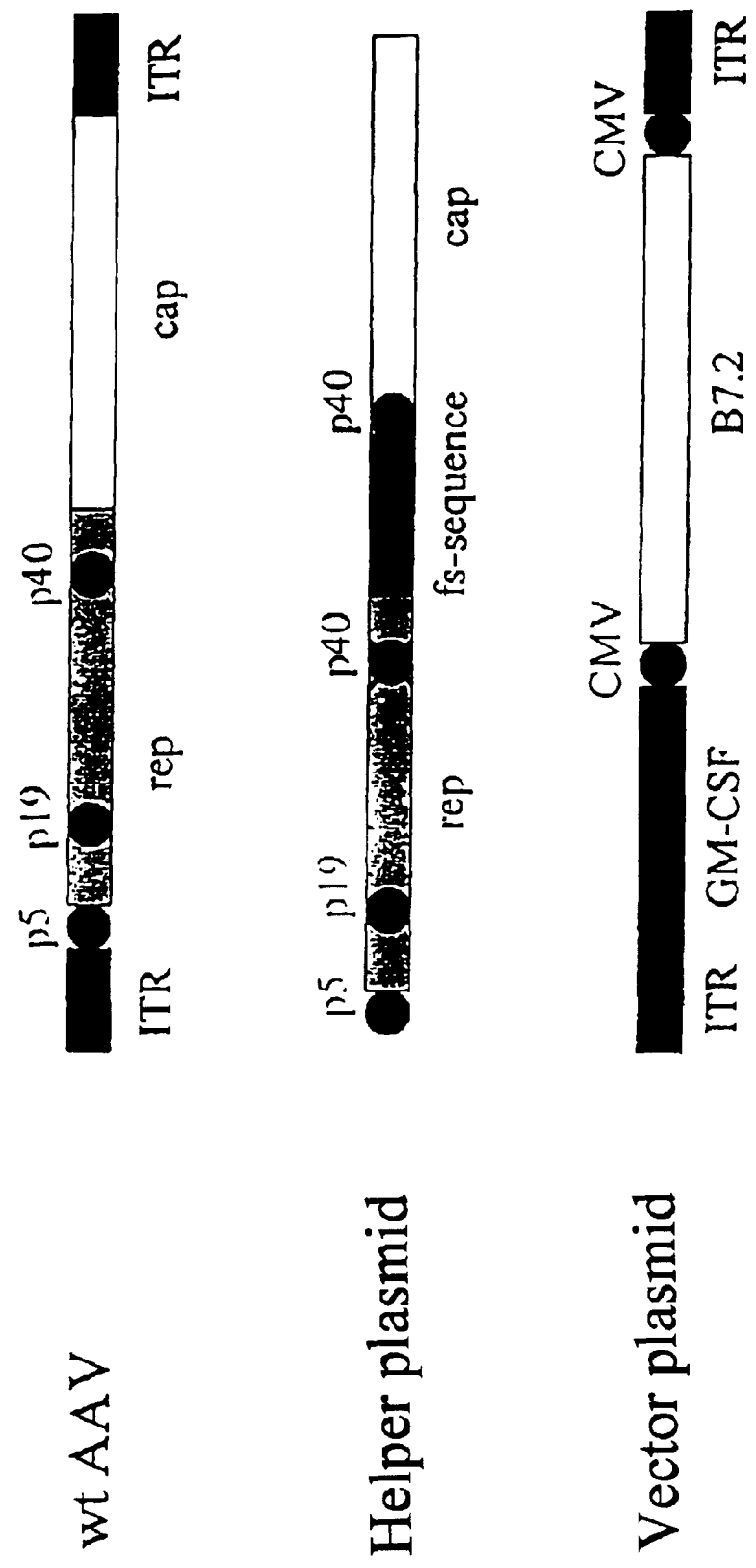
FIG. 3 shows a comparison of the genome structures of wild type AAV (wt AAV), helper construct (=helper plasmid) and vector construct (=vector plasmid).

A bottle of HeLa-t cells ($5 \times 10^6$ cells per bottle per ml) was thawed in a water bath at 37° C. The cells were immediately pipetted dropwise on approx. 10 ml of cold DMEM medium (Dulbecco's modified Eagle's medium) and centrifuged at 200 g for 5 minutes. The cell pellet was resuspended in 10 ml of DMEM and the cells were again pelleted at 200 g. Finally, the cells were suspended in 20 ml of DMEM (with 10% FCS (fetal calf serum), pen/strep (penicillin/streptomycin) and glutamine) and cultured in a Nunc T80 bottle at 37° C., 5% $CO_2$.

2. Preculturing and culturing of HeLa-t cells

A confluent culture bottle was split 1:10 (3 days until confluent again) to 1:20 (4 days until confluent again) to extend the HeLa-t cells and to maintain the bottle size. The cells were split 1:5 to 1:10 when transferred from T80 to T175 bottles. This was carried out by treating the cells with trypsin at 37° C. for about 5 minutes until the cells detached. The detached cells were suspended in an excess of medium (approx. 5 volumes), centrifuged at 200 g for 6 minutes, taken up in fresh medium, if necessary, and distributed into new culture bottles. When using a confluent T80 bottle (first passage of freshly thawed cells) the cells were first treated with trypsin and then 1:10 distributed into five T175 bottles with in each case 50 ml of medium. After three days the cells grew confluent again in the bottles. Then the cells of all five T175 bottles were treated with trypsin and seeded in a tray stack (10 levels, 6320 $cm^2$ of culture area, 900 ml of medium) (approx. $1–2 \times 10^8$ HeLa-t cells). To this end, the tray stack was connected with a sterile glass container via a system of tubes, with the feeding tube to the tray stack initially closed. The glass container was filled with the cell suspension in 900 ml of DMEM. The suspension was then transferred into the tray stack by opening the clamp. The pressure was balanced by using air filters.

3. Preparation of transfection solutions (1) $CaCl_2$ stock solution A 3-molar $CaCl_2$ stock solution was prepared and diluted to 260 mM prior to use and sterile-filtered.

(2) 2×BBS transfection buffer The two times transfection buffer is composed as follows: 280 mM NaCl, 50 mM BES, 0.75 mM $Na_2HPO_4$ and 0.75 mM $NaH_2PO4$ (pH 7.8–8.0).

4. Preparation of vector plasmids

The starting plasmid was plasmid pAV2 (ATCC 37216; Laughlin, L. A. et al. (1983) Gene, 23(1), 65) which contains the AAV genome in a modified pBR322 vector. The integrity of AAV ITRs was checked by sequencing. After hydrolyzing pAV2 with BglII, it was possible to subclone the AAV sequence into pUC19. To this end, pCU19 was cut with BamHI and directly ligated with the AAV-containing BglII fragment of pAV2. The plasmid resulting therefrom is denoted pUCAV2. Sequencing of the ITRs in pUCAV2 and pAV2 revealed that the left ITR is completely intact except for one base exchange at position 2 (T→G), whereas in the right ITR 8 terminal bases are missing.

Subsequently, pUCAV2 was cut with PpuMI and SnaBI, as a result of which the AAV sequences 192 to 4497 which correspond to the AAV expression cassette were removed. These sequences were replaced by a CMV polyA expression cassette from pCI (Promega GmbH, Mannheim, Germany). To this end, firstly PpuMI and EcoRV cleavage sites were introduced by double-strand mutageneses into pCI in front of the CMV promoter and after the polyA cleavage site, and this was done in both orientations (PpuMI in front of CMV and EcoRV after polyA and vice versa). The expression cassette was then cut out of pCI by double hydrolysis with PpuMI and EcoRV and directly cloned in both orientations into the pUCAV2 vector fragment cut with PpuMI, SnaBI (pCI sequences: orientation 1 (CMV at right ITR): (4002 to 4008)+(1 to 1351+5 new bases) and, respectively, orientation 2 (CMV at left ITR): (4001 to 4008)+(1 to 1351)+7 new bases). The different transgenes were subsequently cloned into these base vectors.

Optimum orientation of the expression cassette was determined with the aid of the luciferase reporter gene. The result was that the orientation had obviously no influence on the packaging efficiency of the vector constructs; however, the expression cassette was more active if the CMV promoter is orientated toward the right ITR. In all the cloning and sequencing work it was found that a flop-flop orientation of both ITR structures in the vector plasmids is distinctly more stable than a flip-flop orientation. The flop-flop orientation was much more stable in bacteria and was less frequently susceptible to unwanted recombination events than the flip-flop orientation. A theoretically possible flip-flip orientation was not found in any single clone. For this reason, all transgenes were cloned into a base vector, whose ITRs have flop-flop orientation (FIG. 4).

| Vector plasmid | Orientation of ITRs | Location of CMV promoter | Promoter activity (pAAV-luc) | Promoter activity (rAAV-luc) |
|---|---|---|---|---|
| pAAV-luc Clone 1 | 5'-ITR: flip 3'-ITR: flop | at 5'-ITR | 1.13 | 1.36 |
| pAAV-luc Clone 3 | 5'-ITR: flop 3'-ITR: flop | at 5'-ITR | 1 | 1 |
| pAAV-luc Clones 3b, 11 | 5'-ITR: flip 3'-ITR: flop | at 3'-ITR | 1.37 | 2.54 |
| pAAV-luc Clones 10, 15, 24 | 5'-ITR: flop 3'-ITR: flop | at 3'-ITR | 1.5 | 2.88 |

*=6 µg of vector plasmid were transfected into $4 \times 10^5$ HeLa-t cells. 40 hours after transfection, the cells were lysed and the promoter activity was determined via measuring luciferase counts. The relative promoter activity ($1=2 \times 10^8$ counts) is given.

**=4 µg of vector plasmid were transfected together with 12 µg of helper plasmid (pUC"rep/cap") into $1 \times 10^6$ HeLa-t cells. 2 days later the cells were infected with AdV-5 (MOI=2). 3 days after infection, the cells were disrupted in the medium by freeze-thaw lysis, cell debris was pelleted and the rAAV lysate was heat-inactivated at 60° C. for 10 min. $3 \times 10^5$ irradiated HeLa-t cells (100 Gy) were infected with 10% of the lysate. 40 hours after infecting the cells with rAAV, the cells were lysed and luciferase activity was determined. The relative activity ($1=1 \times 10^6$ counts) is given.

Column 4 (relative promoter activity after transient transfection of constructs) directly reflects and column 5 indirectly reflects the CMV promoter activity as a function of the location within the AAV genome. As can be inferred from the table, the promoter activity increases by about a factor 1.5–3 when said promoter is located at the 3' ITR. The rAAV titers obtained after packaging the various clones are roughly comparable (genomic titers were determined via dotblot analyses). This means that orientation of the ITRs (flip/flop) or of the CMV promoter toward the ITRs plays no part in the ability of the constructs to be packaged into rAAV particles. It should further be mentioned that clones with flip/flop orientation of ITRs (1, 3b and 11) were found very much more infrequently than those with flop/flop orientation.

5. Preparation of the helper plasmid

The AAV bases 190 to 1060 were amplified from wild type AAV DNA by means of PCR. In this connection, the 5' primer was chosen such that a single XbaI cleavage site was introduced at position 199. The PCR fragment was then cut with XbaI and BamHI and cloned into the vector pUC19 which had been cut in the same way. Position 199 in the AAV genome was chosen in order to ensure that all important p5 promoter elements are present in the helper plasmid. After control sequencing, wild type AAV DNA was cut with BamHI and SnaBI and the insert fragment was subsequently cloned into the BamHI and SmaI position of the intermediate. In this way the base helper plasmid pUC "rep/cap" was obtained (FIG. 2). This helper plasmid contains the AAV sequences 201 to 4497, whereas the above-described vector plasmid carries AAV sequences 1 to 191 and, respectively 1–60/83–191 (left ITR) and 4498 to 4671 (right ITR). This way it was ensured that no homologous AAV sequence overlaps are present in the plasmids. Subsequently, Δ37 bases of the 3' end of the AAV genome in pUC "rep/cap", which are not required for optimal expression of the AAV rep and cap genes, was deleted. The resulting helper plasmid is denoted pUC "rep/cap" Δ37 and contains the minimized AAV sequence from position 201 to 4460 (FIG. 2).

Subsequently, the Rep binding site (RBS) in the pUC19 vector backbone (position 684 to 708 inclusive; sequence: 5'-CTCTTCCGTTCCTCGCTCACTGAC-3 (SEQ. ID NO: 2)) was deleted in order to avoid nonhomologous recombination at this position. The plasmid is referred to as pUC "rep/cap" (RBS)Δ37. In some plasmids the three RBS in the rep gene (p5 and p19 promoters) additionally were mutated individually and in various combinations without altering the amino acid sequences of the Rep protein (FIG. 2).

A "functional separation" sequence (fs) of 638 base pairs in length was introduced into another helper plasmid between the rep and cap genes. To this end, first the AAV sequence 1691 to 2328 which comprises the rep C terminus and the AAV p40 promoter including cap sequences and all regulatory sequences essential for p40, was duplicated and cloned after the stop codon for the spliced rep versions (position 2329). As a result, the AAV p40 promoter which controls the cap gene was duplicated and inserted after the rep gene. Subsequently, the p40 promoter in the rep gene was destroyed without altering the Rep amino acid sequence. This was ensured by mutating the p40 TATA box. In total, the following AAV nucleotides were modified for the required cloning steps without altering, however, the Rep and Cap amino acid sequences: 1693 (T→A), 1694 (T→G), 2330 (G→C), 2331 (G→T), 2332 (G→A), 1625 (C→T), 1628 (A→G), 1826 (A→C), 1827 (A→T) and 1828 (G→C). The resulting helper plasmid is denoted pUC "rep/fs/cap"Δ37 (FIG. 2).

Analogously, an additional sequence was inserted into pUC "rep/cap"(RBS)Δ37 resulting in a helper plasmid denoted pUC "rep/fs/cap"(RBS)Δ37 (FIG. 2).

Figure 6:
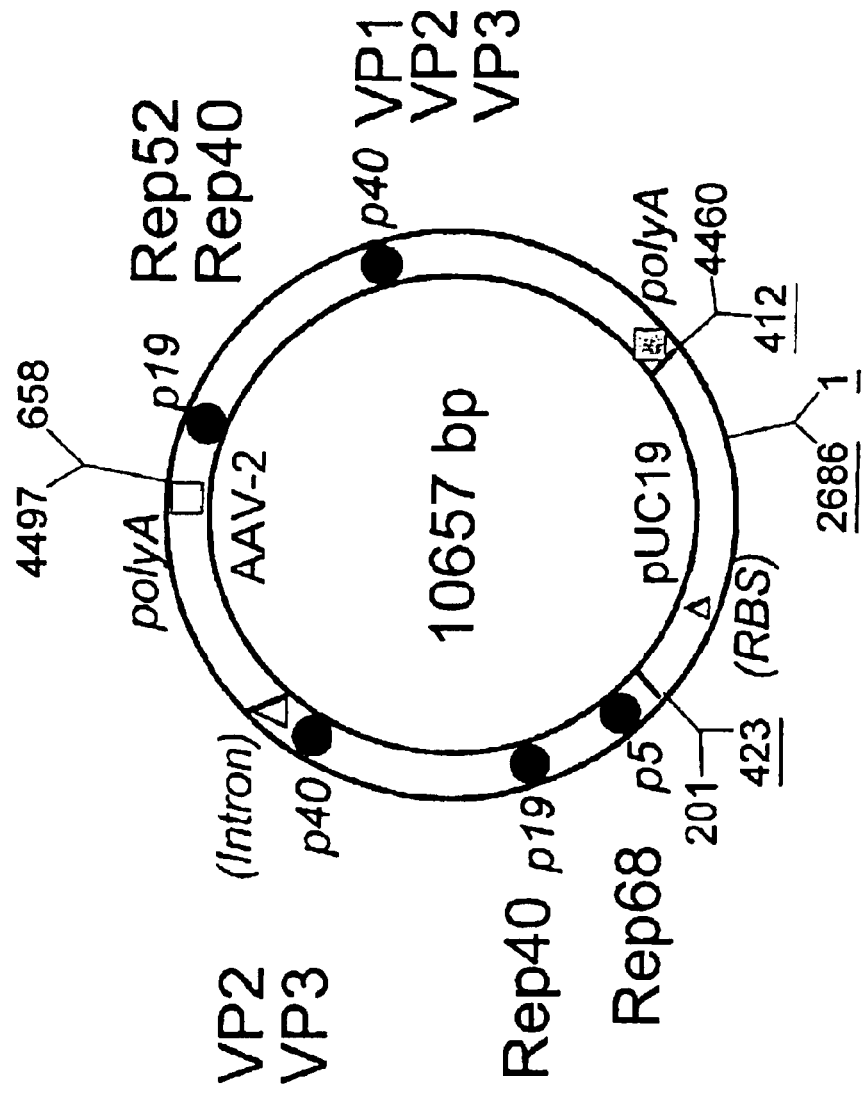
FIG. 6 diagrammatically shows the Rep 78-deficient helper plasmid pUCRep68, 52, 40Cap"(RBS)Δ37.

The other Rep 78-deficient helper constructs were prepared by deleting in the helper construct pUC "rep/cap" (RBS)Δ37 (cf. FIG. 2) AAV nucleotides 1907 to 2227, which correspond to the rep intron, by double-strand mutagenesis, as a result of which plasmid pUCAAVspleiβ was obtained as intermediate. The plasmid pUCAAVspleiβ was linearized with restriction enzyme NdeI, treated with an exonuclease, for example mung bean nuclease (Boehringer Mannheim, Germany), and then the restriction enzyme SphI was added. The fragment obtained in this way, which is 4222 bp long, was linked through a vector fragment by ligation to give the Rep 78-deficient helper construct pUC "Rep68,52, 40Cap"(RBS)Δ37 (10657 bp), (cf. FIG. 6). Said vector fragment can be obtained by using pUC "rep/cap"(RBS) Δ37, for example, which is obtained in a length of 6435 bp after treatment with restriction enzymes NruI and SphI.

Figure 7:
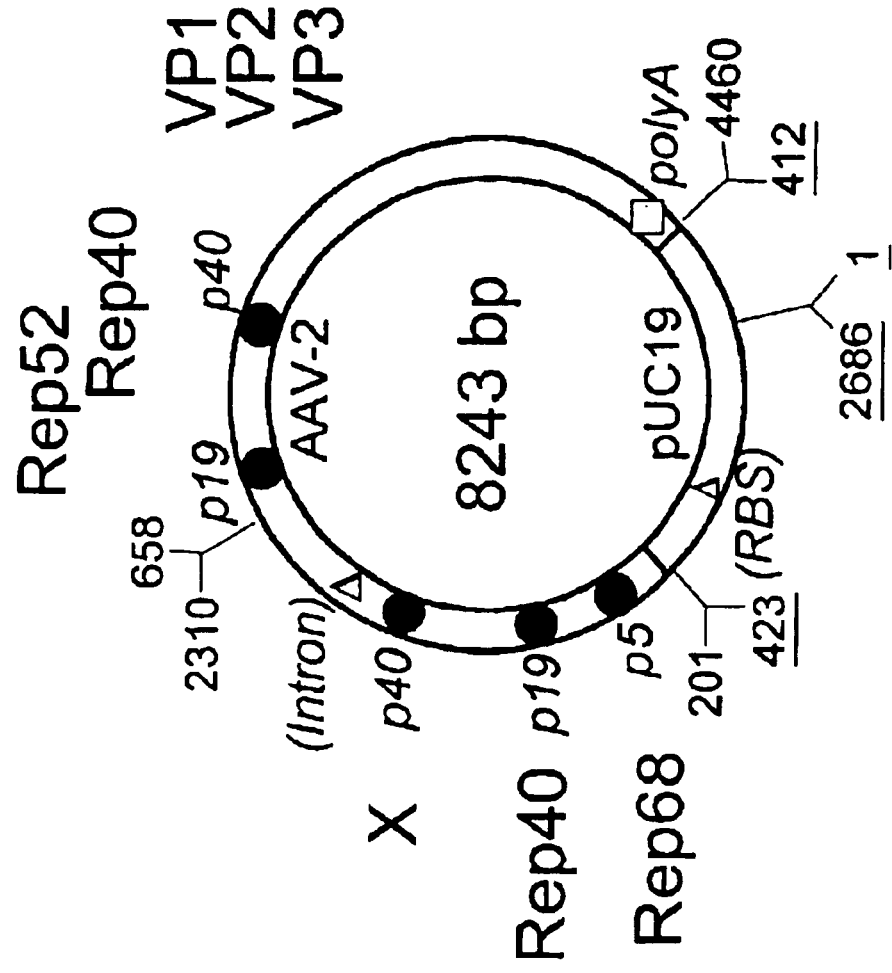
FIG. 7 diagrammatically shows the other Rep 78-deficient helper plasmid pUC"ΔRep78Cap"(RBS)Δ37.
Figure 8:
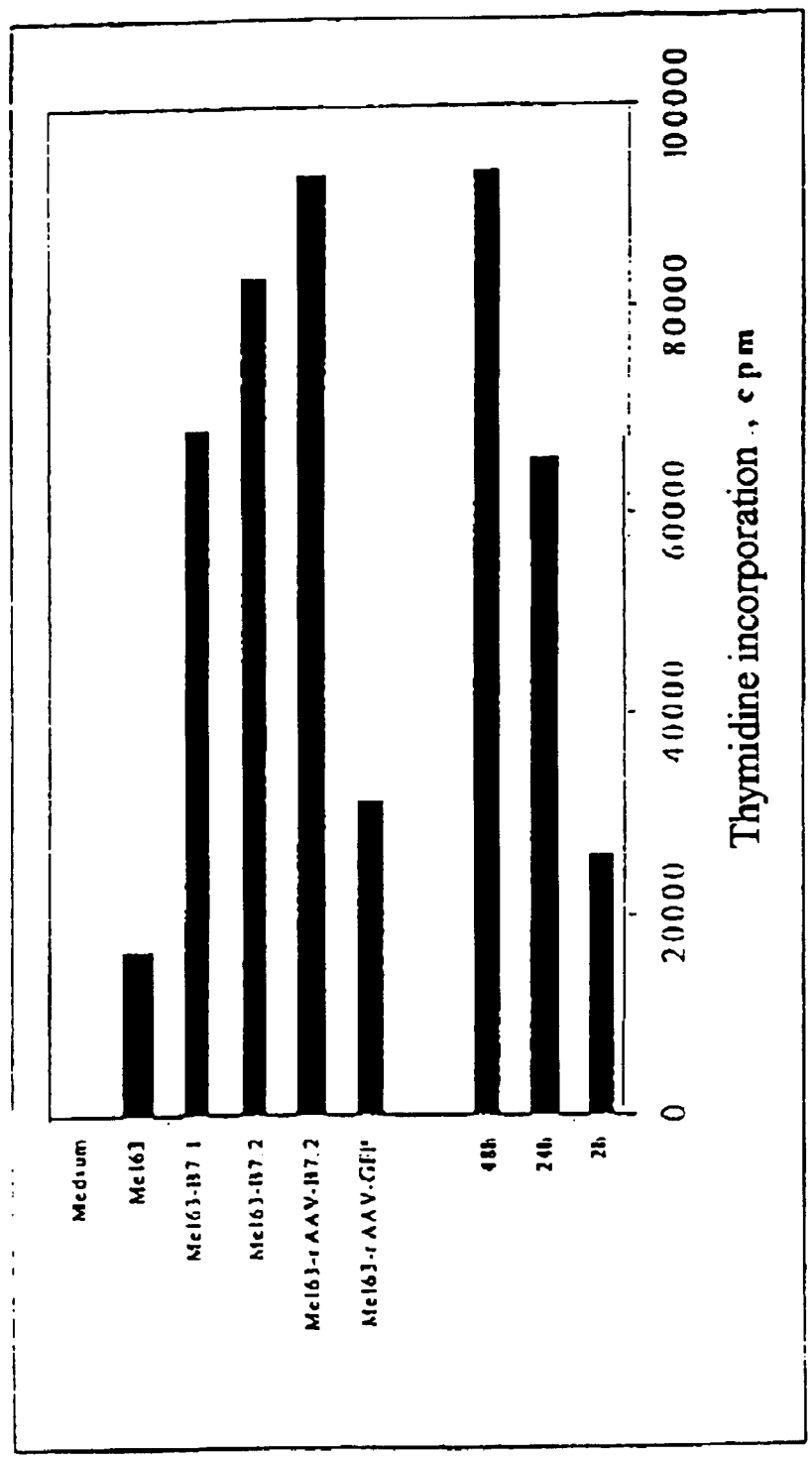
FIG. 8 shows the result of T cell proliferation by transducing Mel63 cells with various constructs coding for B7.1, B7.2 and GFP.

The same vector fragment can furthermore be used for preparing another Rep 78-deficient helper construct pUC "ΔRep78Cap"(RBS)Δ37 (cf. FIG. 7). For this, the intermediate pUCAAVspleiβ was treated with restriction enzymes AseI, BsrBI and SphI. The 1808 bp BsrBI-SphI fragment was linked to the 6435 bp vector fragment by ligation to give said helper construct pUC"ΔRep78Cap"(RBS)Δ37 and a total length of 8243 bp. This cloning strategy partially duplicates the rep gene in both Rep 78-deficient helper constructs so that increased expression of the Rep proteins Rep 68, Rep 52 and Rep 40 from both rep genes is made possible.

All of the above-described helper plasmids which are diagrammatically depicted in FIG. 2 possess roughly comparable packaging capacities.

Within the framework of the cotransfection experiments, 4 μg of vector plasmids (pAAV-GFP) were cotransfected together with 12 μg of helper plasmid into $1 \times 10^6$ HeLa-t cells. Only in the case of the experiment denoted (seq) were first 16 μg of helper plasmid and on the next day 16 μg of vector plasmid sequentially transfected. 2 days after (the first) transfection, the cells were infected with AdV-5 (MOI= 2). 3 days later the cells were disrupted in the medium by freeze/thaw lysis, cell debris was pelleted and the rAAV lysate was heat-inactivated at 60° C. for 10 min. $3 \times 10^5$ irradiated HeLa-t cells (100 Gy) were infected with various dilutions of the lysate. 40 hours after infecting the cells with rAAV, the cells were analyzed in a FACS flow [lacuna] with respect to GFP expression, and from this the transducing rAAV crude lysate titers were determined. Each helper plasmid was assayed in at least 5 independent experiments. The table lists averaged values.

| Helper plasmid | Transducing rAAV-GFP titers (tP/ml) |
| --- | --- |
| pUC "rep/cap" | $1.38 \times 10^7$ |
| pUC "rep/cap"Δ37 | $1.49 \times 10^7$ |
| pUC "rep/fs/cap"Δ37 | $1.26 \times 10^7$ |
| pUC "rep/cap"(RBS)Δ37 | $1.46 \times 10^7$ |
| pUC "rep/fs/cap"(RBS)Δ37 | $9.11 \times 10^6$ |
| pUC "rep/cap"Δ37 (seq) | $2.48 \times 10^7$ | tP = transducing particle
seq = sequential transfection

Packaging and titer determination for the experiments 1 to 3 below was carried out as described above. Experiments 1 and 3 were sequential transfections, and experiment 2 was a cotransfection of helper construct and vector construct.

In the sequential transfection of helper construct and vector construct (experiments 1 and 3, depicted in the table below), Rep 78-deficient helper constructs show to some degree equally good packaging efficiencies compared with Rep 78-coding helper constructs. All transducing titers were in the same logarithmic region. Cotransfections were carried out in experiment 2, as a result of which other experimental conditions were chosen, and it is therefore impossible to compare experiment 2 with experiments 1 and 3, also with respect to packaging efficiencies. The results of these experiments are shown in the following table.

| Helper construct | Experiment 1 transd. titer (tP/ml) | Experiment 2 transd. titer (tP/ml) | Experiment 3 transd. titer (tP/ml) |
| --- | --- | --- | --- |
| pUC "rep/cap"Δ37 | 4.87E+06 | 7.80E+07 | 4.90E+07 |
| pUC "rep/cap"(RBS)Δ37 | 8.13E+06 | 2.60E+07 | 3.80E+07 |
| pUC "rep/fs/cap"Δ37 | 7.26E+06 | 2.50E+07 | 4.10E+07 |
| pUC "rep/fs/cap"(RBS)Δ37 | 2.74E+06 | 3.50E+06 | 5.20E+07 |
| pUC "Rep68, 52, 40Cap" (RBS)Δ37 | 1.98E+06 | 2.50E+06 | 2.40E+07 |
| pUC "ΔRep78Cap"(RBS)Δ37 | n.d. | 2.50E+06 | 1.80E+07 |

6. Packaging of recombinant AAV vectors

Day 1: Seeding of HeLa-t cells in tray stacks

1 Nunc tray stack (10 levels, 6320 cm² of culture area) was filled with approx. 2×10⁸ HeLa-t cells in 900 ml of DMEM, as already described in more detail above, and cultured overnight at 37° C., 5% $CO_2$.

Day 2: Calcium phosphate transfection of HeLa-t cells with the helper plasmid, according to Chen, T. & Okayama, H. (1987), supra:

1800 µg of helper plasmid were mixed with 45 ml of sterile 260 mM $CaCl_2$, 45 ml of sterile 2×BBS were added, mixed carefully and incubated at room temperature for 15 min. The medium was then transferred from the tray stack into a sterile vessel of 1 to 2 l in size, the transfection mixture was added by pipetting and the medium was fed back again into the tray stack. The transfection was carried out overnight at 35° C., 3% $CO_2$.

Day 3: Transfection of HeLa-t cells with the vector plasmid:

18 hours after transfection with the helper plasmid, the cells were adjusted to 37° C., 5% $CO_2$, and after a further 3 to 5 hours the medium was replaced with a new medium (900 ml of DMEM with 10% FCS, glutamine and pen/strep) and the vector plasmid was transferred into the fresh medium, as already described in more detail for the helper plasmid above.

Day 4: Infection of HeLa-t cells with adenoviruses:

18 hours after transfection with the vector plasmid, the cells were again adjusted to 37° C., 5% $CO_2$ and, after a further 3 to 5 hours, infected with adenoviruses. To this end, the culture medium was replaced with 900 ml of DMEM medium (DMEM with 10% FCS, glutamine and pen/strep) to which 2 to 3×10⁹ (MOI=5) adenoviruses (Ad-5) were added. Culturing was then carried out overnight at 37° C., 5% $CO_2$.

Day 5: Change of medium

On the next day, the culture medium was replaced by 900 ml of DMEM medium (with glutamine, pen/strep and gentamicin, but without FCS).

Day 8: Harvest of rAAV particles

On the eighth day the rAAV particles were harvested.

The rAAV particles are harvested by freezing at =20° C. and thawing again at 4° C. the complete tray stack three times in succession. The lysate is transferred into sterile centrifuge beakers and cell debris is removed by centrifugation at 5000 g. The clear lysate is then starting material for subsequent purification steps.

7. T-cell activation by B7.2-transduced melanoma cells

The melanoma cell line Mel63 was irradiated (100 Gy) and transduced with rAAV-B7.2. After 48 hours, the transduced melanoma cells (Mel63-rAAV-B7.2, 10⁴ per well) were incubated with peripheral blood lymphocytes (10⁵ per well) of a healthy donor. Lymphocytes proliferation was measured by means of radioactive thymidine incorporation on day 5. B7.2 transduction caused T cell activation, whereas T lymphocytes do not proliferate without stimulation (medium) or after incubation with unmodified Mel63 cells (Mel63). Said reaction was as strong as the one observed after incubating the T lymphocytes with stably expressing B7.1⁺ and B7.2⁺ variants of the melanoma cell lines Mel63.

What is claimed is:

1. A helper construct comprising a nucleic acid sequence coding for at least one Rep protein controlled by its natural promoter p5, p19, and/or p40, wherein the helper construct, with the exception of the AAV promoters, does not comprise a Rep binding site, and the helper construct lacks nucleic acid sequence encoding Rep 78.

2. The helper construct as claimed in claim 1, wherein the construct does not comprise SEQ ID NO: 1 in the vector backbone.

3. The helper construct as claimed in claim 1, wherein the construct includes nucleic acid sequence coding for at least one Rep protein selected from Rep 68, Rep 52, and Rep 40 and, wherein the construct comprises nucleic acid sequences coding for Cap proteins VP 1, VP 2, and VP 3.

4. The helper construct as claimed in claim 3, wherein the nucleic acid sequence codes for Rep 68 and Rep 52.

5. The helper construct as claimed in claim 1, wherein nucleic acid sequence codes for Rep 68 and Rep 52.

6. The helper construct as claimed in claim 1, wherein an additional nucleic acid sequence which impairs packaging of the helper construct into an AAV capsid is incorporated between the nucleic acid sequence coding for Rep and a nucleic acid sequence within the helper construct that encodes an AAV Cap protein.

7. The helper construct as claimed in claim 6, wherein the additional nucleic acid sequence is at least approximately 300 nucleotides in length.

8. The helper construct as claimed in claim 6, wherein the additional nucleic acid sequence is at least approximately 500 nucleotides in length.

9. The helper construct as claimed in claim 6, wherein the additional nucleic acid sequence is approximately 600 to approximately 700 nucleotides in length.

10. The helper construct as claimed in claim 1, wherein the AAV is AAV-2 and bases 4461–4497 of AAV-2 have been deleted.

11. The construct as claimed in claim 1, wherein the construct is replication-deficient.

12. The construct as claimed in claim 1, wherein the construct is self-replicating.

13. The construct as claimed in claim 12, wherein the construct comprises both SV40ori nucleic acid sequences and nucleic acid sequences coding for the SV40 T antigen.

14. The construct as claimed in claim 12, wherein the construct comprises both EBV oriP nucleic acid sequences and EBV EBNA sequences.

15. A method of producing rAAV, said method comprising introducing at least one helper construct as claimed in claim 1 and a vector construct into a suitable cell and incubating the cell until rAAV is produced.

16. The helper construct as claimed in claim 1, which comprises nucleic acid sequences coding for the Cap proteins.

17. The helper construct as claimed in claim 16, wherein the construct does not comprise SEQ ID NO: 1 in the vector backbone.

18. The helper construct as claimed in claim 16, wherein the construct includes nucleic acid sequence coding for at least one Rep protein selected from Rep 68, Rep 52, and Rep 40 and, wherein the construct comprises nucleic acid sequences coding for Cap proteins VP 1, VP 2, and VP 3.

19. The helper construct as claimed in claim 18, wherein the nucleic acid sequence codes for Rep 68 and Rep 52.

20. The helper construct as claimed in claim 16, wherein the AAV is AAV-2 and bases 4461–4497 of AAV-2 have been deleted.

21. The helper construct as claimed in claim 16, wherein the construct is replication-deficient.

22. The helper construct as claimed in claim 16, wherein the construct is self-replicating.

23. The helper construct as claimed in claim 22, wherein the construct comprises both SV40ori nucleic acid sequences and nucleic acid sequences coding for the SV40 T antigen.

24. The helper construct as claimed in claim 22, wherein the construct comprises both EBV oriP nucleic acid sequences and EBV EBNA sequences.

25. A method of producing rAAV, said method comprising introducing at least one helper construct as claimed in claim 16 and a vector construct into a suitable cell and incubating the cell until rAAV is produced.

26. A composition comprising the AAV helper construct as claimed in claim 1 and an AAV vector construct, wherein the helper construct does not comprise an nucleic acid sequences which are homologous to the vector construct and which allow homologous recombination with the vector construct when co-transfected.

27. A composition comprising the AAV helper construct as claimed in claim 16 and an AAV vector construct, wherein the helper construct does not comprise an nucleic acid sequences which are homologous to the vector construct and which allow homologous recombination with the vector construct when co-transfected.

* * * * *

UNITED STATES PATENT AND TRADEMARK OFFICE
CERTIFICATE OF CORRECTION

PATENT NO.    : 6,846,665 B1
DATED         : January 25, 2005
INVENTOR(S)   : Hörer et al.

It is certified that error appears in the above-identified patent and that said Letters Patent is hereby corrected as shown below:

<u>Column 11</u>
Line 2, replace "pUCRep68, 52, 40Cap" (RBS) Δ37" with -- pUC"Rep68, 52, 40Cap" (RBS) Δ37 --.

Signed and Sealed this

Seventeenth Day of May, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthetic RBS Consensus Sequence

<400> SEQUENCE: 1
cgcttcctcg ctcactga                                             18

<210> SEQ ID NO 2
<211> LENGTH: 25
<212> TYPE: DNA
<213> ORGANISM: Artificial Sequence
<220> FEATURE:
<223> OTHER INFORMATION: Synthetic RBS Binding Site

<400> SEQUENCE: 2
ctcttccgct tcctcgctca ctgac                                     25